(12) United States Patent
Yee et al.

(10) Patent No.: US 6,603,000 B2
(45) Date of Patent: Aug. 5, 2003

(54) SYNTHESIS FOR HETEROARYLAMINE COMPOUNDS

(75) Inventors: Nathan Yee, Danbury, CT (US); Suresh R. Kapadia, Danbury, CT (US); Jinhua J. Song, Hopewell Junction, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 13 days.

(21) Appl. No.: 09/902,085

(22) Filed: Jul. 11, 2001

(65) Prior Publication Data

US 2003/0028017 A1 Feb. 6, 2003

(51) Int. Cl.$^7$ ..................... C07D 413/00; C07D 421/00
(52) U.S. Cl. ........................ 544/124; 546/256
(58) Field of Search .................... 544/124; 546/256

(56) References Cited

U.S. PATENT DOCUMENTS 5,498,755 A  *  3/1996  Chandraratna et al. ..... 564/272
5,502,059 A     3/1996  Labeeuw et al.

FOREIGN PATENT DOCUMENTS

| WO | WO 98/52558 | 11/1998 |
| WO | WO 99/23091 | 5/1999 |
| WO | WO 00/55139 | 9/2000 |

OTHER PUBLICATIONS

Kurita, K. et al; Trichloromethyl Chloroformate, Reaction with Amines, Amino Acids and Amino Alcohols, J. Org. Chem., vol. 41, No. 11, 1976 pp 2070–2071.

Thavonekham, B. et al; A Practical Synthesis of Ureas from Phenyl Carbamates; Synthesis, Oct. 1997 pp 1189–1194.

Patonay, T. et al; α Haloalkyl Haloformates and Related Compound 3$^1$ A Facile Synthesis of Symmetrical and Unsymmetrical Ureas via Chloromethyl Carbamates; Synthetic Commuinications 26(22) 4253–4265 (1996).

Majer, P. et al; A Safe and Efficient Method for Preparation of N, N'–Unsymmetrically Disubstituted Ureas Utilizing Triphosgene, J. Org. Chem. 1994, 59, vol. 7 1937–1938.

* cited by examiner

*Primary Examiner*—John M. Ford
*Assistant Examiner*—Tamthom N. Truong
(74) *Attorney, Agent, or Firm*—Robert P. Raymond; Anthony P. Bottino; Alan R. Stempel

(57) ABSTRACT

Disclosed is a novel method of producing heteroaryl amines of the formula(I):

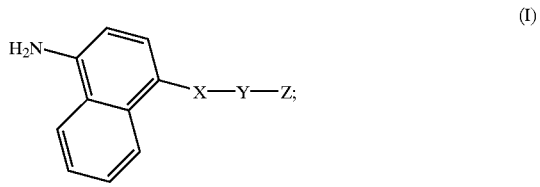

(I)

wherein X, Y and Z are described herein, the heteroarylamines are useful in the production of heteroaryl ureas which are key component in pharmaceutically active compounds possessing a heteroaryl urea group.

5 Claims, No Drawings

SYNTHESIS FOR HETEROARYLAMINE COMPOUNDS

FIELD OF INVENTION

This invention relates to the synthesis of heteroarylamine compounds which are useful in the production of heteroaryl ureas a key component in pharmaceutically active compounds possessing a heteroaryl urea group.

BACKGROUND OF THE INVENTION

Aryl- and heteroaryl-substituted ureas have been described as inhibitors of cytokine production. These inhibitors are described as effective therapeutics in cytokine-mediated diseases, including inflammatory and autoimmune diseases. Examples of such compounds are reported in WO 99/23091 and in WO 98/52558.

A key step in the synthesis of these compounds is the formation of the urea bond. Various methods have been reported to accomplish this. For example, as reported in the above references, an aromatic or heteroaromatic amine, $Ar_1NH_2$, may be reacted with an aromatic or heteroaromatic isocyanate, $Ar_2NCO$, to generate the urea $Ar_1HC(O)NHAr_2$.

Scheme I

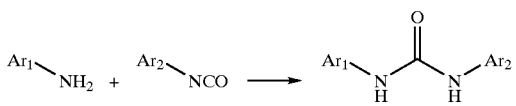

If not commercially available, one may prepare the isocyanate by reaction of an aryl or heteroaryl amine $Ar_2$—$NH_2$ with phosgene or a phosgene equivalent, such as bis(trichloromethyl) carbonate (triphosgene) (P. Majer and R. S. Randad, J. Org. Chem. 1994, 59, 1937) or trichloromethyl chloroformate (diphosgene) (K. Kurita, T. Matsumura and Y. Iwakura, J. Org. Chem. 1976, 41, 2070) to form the isocyanate $Ar_2$—NCO, followed by reaction with $Ar_1NH_2$ to provide the urea. Other approaches to forming the urea reported in the chemical literature include reaction of a carbamate with an aryl or heteroaryl amine, (see for example B. Thavonekham, Synthesis, 1997, 1189 and T. Patonay et al., Synthetic Communications, 1996, 26, 4253) as shown in Scheme II. U.S. Provisional Application No. 60/143,094 also discloses a process of making heteroaryl ureas by reacting particular carbamate intermediates with the desired arylamine.

Scheme II

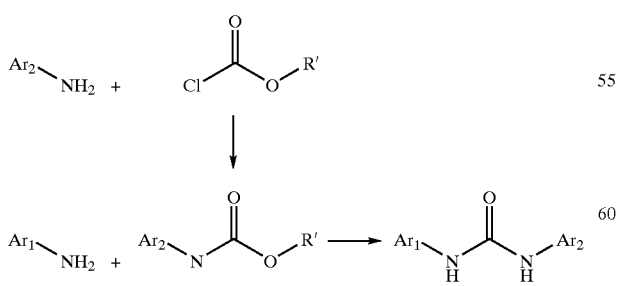

U.S. application Ser. No. 09/505,582 and PCT/US00/03865 describe cytokine inhibiting ureas of the following formula:

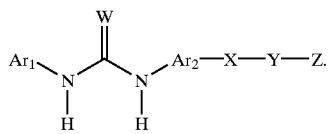

An intermediate required to prepare preferred compounds described therein has a 1,4-disubstituted naphthalene as $Ar_2$ and is illustrated in the formula below.

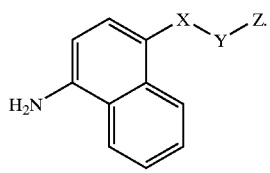

The preparation of these intermediates require the coupling of the naphthyl ring with X. Preferred X include aryl and heteroaryl groups. Previously described methods, including U.S. application Ser. No. 09/505,582 and PCT/US00/03865 achieve the coupling of these aromatic residues by using a coupling reaction catalyzed by a transition metal, such as palladium, in the presence of a ligand, such as triphenyl phosphine. Coupling methods include Stille coupling, requiring the preparation of a tributylstannyl intermediate, or a Suzuki coupling, requiring the preparation of a boronic acid intermediate (Scheme III).

Scheme III $M = Sn(Bu)_3$ or $B(OH)_2$

Some steps in these methods require cooling to extreme temperatures (−78° C.). Others require reaction under high pressure, require chromatography to purify the product, or use expensive reagents. For these reasons, these methods are not suitable for large-scale or industrial-scale production.

SUMMARY OF THE INVENTION

It is an object of the invention to provide a novel method of producing heteroaryl amines of the formula(I):

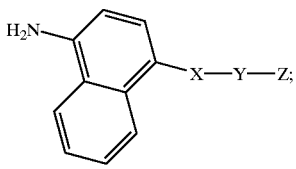

(I)

wherein X, Y and Z are described below, the heteroarylamines are useful in the production of heteroaryl ureas as mentioned above.

DETAILED DESCRIPTION OF THE INVENTION

Disclosed herein is a novel process for preparing preferred heteroarylamine intermediates including those heteroarylamine intermediates described in U.S. application Ser. No. 09/505,582, and PCT/US00/03865. The processes described herein have several advantages. They use inexpensive starting materials and reagents, the reactions are run at moderate temperatures, there are no high-pressure reactions and chromatography is not required.

The novel feature of the invention is the construction of naphthalene ring, as exemplified in Scheme I below, from the appropriately substituted carboxylic acid 5, which in turn was synthesized beginning from a novel ester of the formula (II) and a diester such as diethyl succinate. Any of the compounds of the formula (II) as described herein can be synthesized from readily available and cost efficient starting materials such as example 1 below.

This invention provides a novel strategy for the synthesis of heteroarylamine compounds of the formula (I):

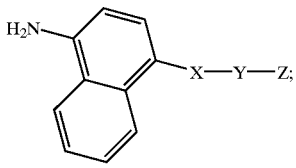

(I)

wherein:
the naphthyl ring is further optionally substituted by one or more $R_1$ or $R_2$;
X is chosen from
a $C_{5-8}$ cycloalkyl and cycloalkenyl optionally substituted with one to two oxo groups or one to three $C_{1-4}$ alkyl, $C_{1-4}$ alkoxy or $C_{1-4}$ alkylamino chains each being branched or unbranched;
aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl and pyrazinyl; each being optionally independently substituted with one to three $C_{1-4}$ alkyl, $C_{1-4}$alkoxy, hydroxy, nitro, nitrile, amino, mono- or di-($C_{1-3}$ alkyl)amino, mono- or di-($C_{1-3}$ alkylamino) carbonyl, $NH_2C(O)$, $C_{1-6}$ alkyl-S(O)$_m$ or halogen;
Y is chosen from
a bond and a $C_{1-4}$ saturated or unsaturated branched or unbranched carbon chain optionally partially or fully halogenated, wherein one or more methylene groups are optionally replaced by O, N, or S(O)$_m$ and wherein Y is optionally independently substituted with one to two oxo groups, phenyl or one or more $C_{1-4}$ alkyl optionally substituted by one or more halogen atoms;
Z is chosen from
phenyl, pyridinyl, pyrimidinyl, pyridazinyl, pyrazinyl, imidazolyl, pyrazolyl, triazolyl, tetrazolyl, furanyl, thienyl, pyranyl, each being optionally substituted with one to three halogen, $C_{1-6}$ alkyl, $C_{1-6}$ alkoxy, hydroxy, amino, mono- or di-($C_{1-3}$ alkyl)amino, $C_{1-6}$ alkyl-S(O)$_m$, CN, CONH$_2$, COOH or phenylamino wherein the phenyl ring is optionally substituted with one to two halogen, $C_{1-6}$ alkyl or $C_{1-6}$ alkoxy;
tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, thiomorpholinyl sulfonyl, piperidinyl, piperidinonyl, piperazinyl, tetrahydropyrimidonyl, cyclohexanonyl, cyclohexanolyl, pentamethylene sulfidyl, pentamethylene sulfoxidyl, pentamethylene sulfonyl, tetramethylene sulfide, tetramethylene sulfoxidyl or tetramethylene sulfonyl each being optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, CONH$_2$, phenylamino-$C_{1-3}$ alkyl or $C_{1-3}$ alkoxy-$C_{1-3}$ alkyl;
halogen, $C_{1-4}$ alkyl, nitrile, amino, hydroxy, $C_{1-6}$ alkoxy, $NH_2C(O)$, mono- or di-($C_{1-3}$alkyl) aminocarbonyl, mono- or di-($C_{1-3}$alkyl)amino, secondary or tertiary amine wherein the amino nitrogen is covalently bonded to $C_{1-3}$ alkyl or $C_{1-5}$ alkoxyalkyl, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, carboxamide-$C_{1-3}$ alkyl, phenyl, wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$, or phenyl-S(O)$_m$, wherein the phenyl ring is optionally substituted with one to two halogen, $C_{1-6}$ alkoxy, hydroxy, halogen or mono- or di-($C_{1-3}$ alkyl)amino;
$C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;
$R_1$ and $R_2$ are independently chosen from:
a $C_{1-6}$ branched or unbranched alkyl optionally partially or fully halogenated, $C_{1-4}$ branched or unbranched alkoxy, each being optionally partially or fully halogenated, halogen, $C_{1-3}$ alkyl-S(O)$_m$ optionally partially or fully halogenated and phenyl-sulfonyl;
and
m is 0, 1 or 2.

The process of the invention in its broadest generic aspect is provided below and exemplified in a non-limiting embodiment shown in Scheme 1:
said process comprising:
a) reacting a Z—Y—X—COO—$R_x$ ester (II) wherein $R_x$ is $C_{1-5}$alkyl or aryl with a di-alkyl or diaryl ester (III) in a suitable solvent protic or aprotic, polar or nonpolar, preferably aprotic such as THF, DME, DMSO, ether, dioxane, CH$_2$Cl$_2$, CHCl$_3$, toluene, pyridine or DMF, or suitable alcohols, preferably the solvent is chosen from THF and DMSO, more preferably THF, and a suitable base such as organic or inorganic bases such as NaH, NaNH$_2$, sodium alkoxides such as Na-t-butoxide, Na-ethoxide, NaOH, pyridine, TEA, DBU or BuLi, preferably NaH or Na t-butoxide, and optionally where appropriate as in Example 3, in the presence of an additive such as DMPU and HMPA, preferably DMPU, under the temperature of about 0 to 200° C. for a reaction time of about 5 min to 24 h, preferably when using the preferred solvent THF at 60–70° C. for about 8 h and isolating the compound intermediate (IV). Examples 1 & 2 are representative methods for preparation of compounds of the formula(II), methods of preparing other compounds of the formula(II) is within the skill in the art.

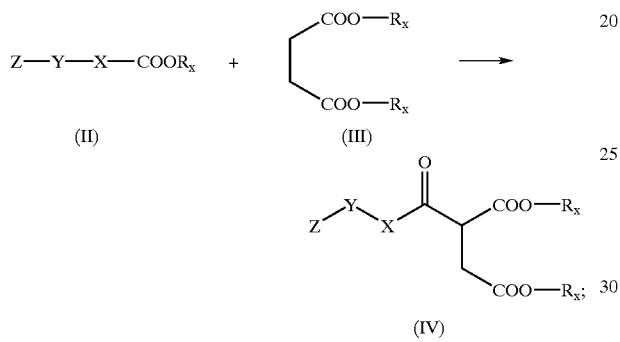

b) subjecting the product of step a) to acidic or basic hydrolysis, preferably acidic hydrolysis, and decarboxylation under suitable acid conditions apparent to those skilled in the art, such as conc. H$_2$SO$_4$ in HOAc at a temperature of about 50 to 200° C. and for about 5 min to 24 hours, preferably about 100° C. for about 7 h; followed by esterification under appropriate conditions with a C$_{1-5}$alcohol, preferably EtOH; subsequent phenyl nucleophilic addition via for example a phenyl Grignard reagent PhMgBr, phenylLi, phenylZnCl, preferably phenyl Grignard, the phenyl being optionally substituted by R$_1$ and/or R$_2$; reductive cleavage under appropriate conditions such as HCOONH$_4$/Pd/C/EtOH to form a carboxylic acid compound which on treatment with a strong mineral acid such as H$_2$SO$_4$, HCl, MeSO$_3$H, CF$_3$SO$_3$H, PPA or Lewis acid such as SnCl$_4$, AlCl$_3$, BF$_3$—OEt$_2$ and Yb(OTf)$_2$, preferably PPA, optionally in a suitable solvent at RT to 200° C., preferably about 110° C., to form a product intermediate of the formula(V), and isolating the product:

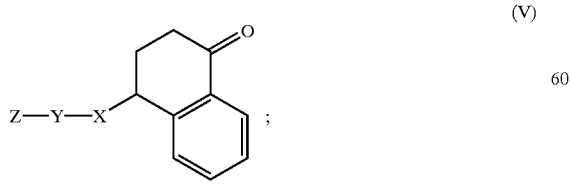

c) reacting the product from step b) with HNR$_y$R$_z$ or it's respective salt thereof, to form an enamine or imine, preferably an oxime, compound of the formula(VI) under suitable conditions.

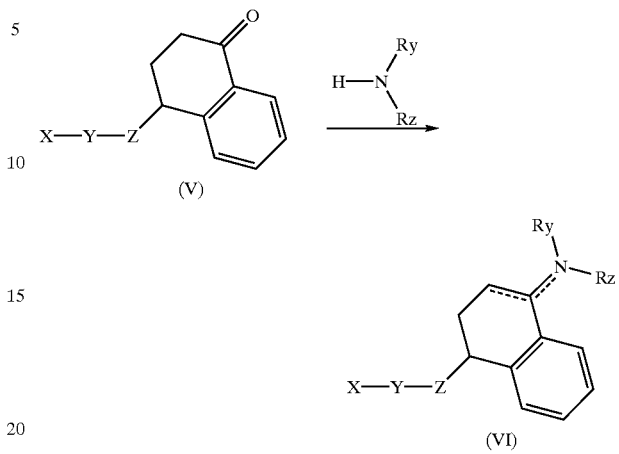

wherein R$_y$ is C$_{1-5}$alkyl or hydrogen, R$_z$ is C$_{1-5}$alkyl, hydrogen or OH with the proviso that when formula (VI) is an enamine tautomer then R$_y$ and R$_z$ are both C$_{1-5}$alkyl, or when formula (VI) is an imine tautomer then R$_z$ is OH, C$_{1-5}$alkyl or hydrogen and R$_y$ is not present:

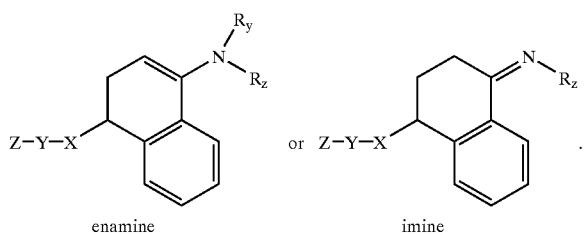

In a preferred but nonlimiting embodiment, forming an oxime by adding NH$_2$OH.HCl (where R$_y$ is H and R$_z$ is OH) in a suitable solvent such as EtOH with a suitable base such as NaOH at about RT for about 1 to 24 h, preferably 18 h;

c) 1) where the product of step c) is an imine, preferably an oxime (R$_y$=H, R$_z$=OH), preferably in a one pot reaction acylating and reducing the product of step c) under conditions known in the art, a preferred but non-limiting example is acetylating/reducing conditions, such as treating compound (VI) with acetic anhydride, acetic acid and a suitable reducing agent such as Fe, SnCl$_2$ and Zn, preferably Fe, at about 55° C. for about 5 hours; then treating the unsaturated amide product (8) under oxidizing conditions capable of forming the naphthalene ring of the formula(I) above, for example, treating the amide product(8) with an oxidizing reagant such as DDQ, O$_2$, CrO$_3$ and KMnO$_4$, preferably DDQ, in a non-polar solvent such as methylene chloride, at about 0 to 50° C., preferably RT for about 0.5 to 10 h, preferably 5 h; followed by deprotection by methods known in the art to provide the formation of formula (I):

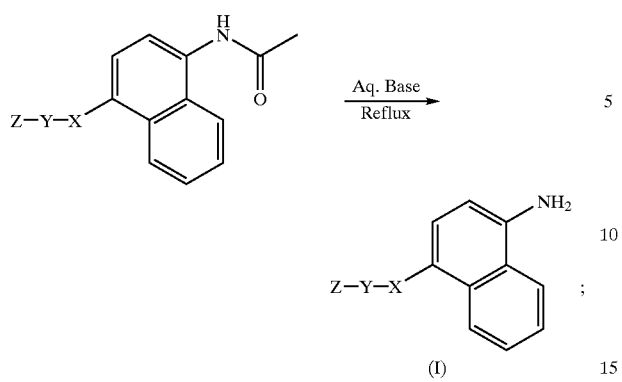

or 2) where the product of step c) is an enamine, oxidizing the enamine under suitable oxidizing conditions to form the naphthalene ring, then deprotecting the nitrogen to form the amine of the formula (I). In a non-limiting example, $R_y$ and $R_z$ are benzyl, oxidation to the naphthalene ring may be accomplished as described above, and debenzylation may be accomplished by methods known to those skilled in the art, for example $H_2$/palladium/C.

Compounds of the formula (I) possessing a particularly desired Ar—X—Y—Z combination can be synthesized without undue experimentation by variations apparent to those of ordinary skill in the art in view of the teachings in this specification and the state of the art. More specific examples of possible X—Y—Z combinations are to be found in PCT application no. PCT/US00/03865 and U.S. application Ser. No. 09/505,582 each of which is incorporated herein by reference in their entirety.

In another embodiment of the invention there is provided a novel process of making compounds of the formula(I) as described above and wherein:

X is chosen from
  a $C_{5-8}$ cycloalkyl and cycloalkenyl optionally substituted with one to two oxo groups or one to three $C_{1-4}$ alkyl, $C_{1-4}$ alkoxy or $C_{1-4}$ alkylamino chains each being branched or unbranched;
  aryl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl and pyrazinyl; each being optionally independently substituted with one to three $C_{1-4}$ alkyl, nitro, nitrile, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is chosen from
  a bond and
  a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms;

Z is chosen from:
  phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, hydroxy, amino, mono- or di-($C_{1-3}$ alkyl)amino or $CONH_2$;
  tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, hydroxy, amino, mono- or di-($C_{1-3}$ alkyl)amino or $CONH_2$;
  nitrile, $C_{1-6}$ alkyl-$S(O)_m$, halogen, hydroxy, $C_{1-4}$ alkoxy, amino, mono- or di-($C_{1-6}$ alkyl)amino, mono- or di-($C_{1-3}$ alkyl)aminocarbonyl and $NH_2C(O)$.

In yet another embodiment of the invention there is provided a novel process of making compounds of the formula(I) as described immediately above and wherein:

X is chosen from
  aryl, pyridinyl, pyrimidinyl, benzimidazole, 3H-imidazo[4,5-b]pyridine, piperazinyl, pyridazinyl and pyrazinyl; each being optionally independently substituted with one to three $C_{1-4}$ alkyl, nitro, nitrile, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is chosen from
  a bond and
  a $C_{1-4}$ saturated carbon chain wherein one of the carbon atoms is optionally replaced by O, N or S and wherein Y is optionally independently substituted with an oxo group;

Z is chosen from
  phenyl, pyridinyl, pyrimidinyl, pyridazinyl, pyrazinyl, imidazolyl, dihydrothiazolyl, dihydrothiazolyl sulfoxide, pyranyl and pyrrolidinyl which are optionally substituted with one to two $C_{1-2}$ alkyl or $C_{1-2}$ alkoxy;
  tetrahydropyranyl, morpholinyl, thiomorpholinyl, thiomorpholinyl sulfoxidyl, piperidinyl, piperidinonyl, piperazinyl and tetrahydropyrimidonyl which are optionally substituted with one to two $C_{1-2}$ alkyl or $C_{1-2}$ alkoxy; and $C_{1-3}$ alkoxy.

In yet still another embodiment of the invention there is provided a novel process of making compounds of the formula(I) as described immediately above and wherein:

X is chosen from
  pyridinyl and pyrimidinyl, each being optionally independently substituted with one to three $C_{1-4}$ alkyl, nitro, nitrile, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is chosen from
  a bond,

—$CH_2$—, —$CH_2CH_2$—, —$C(O)$—, —$O$—, —$S$—, —$NH$—$CH_2CH_2CH_2$—, —$N(CH_3)$— and —$NH$—;

In yet a further embodiment of the invention there is provided a novel process of making compounds of the formula(I) as described immediately above and wherein:

Y is chosen from

—$CH_2$—, —$NH$—$CH_2CH_2CH_2$— and —$NH$— and

Z is morpholinyl.

All terms as used herein in this specification, unless otherwise stated, shall be understood in their ordinary meaning as known in the art. For example, "$C_{1-6}$alkoxy" is a $C_{1-6}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "aryl" as used herein shall be understood to mean aromatic carbocycle or heteroaryl as defined herein.

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle", unless otherwise noted, refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl", unless otherwise noted, shall be understood to mean an aromatic 5–8 membered monocyclic or 8–11 membered bicyclic ring containing 1–4 heteroatoms such as N, O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl.

Terms which are analogs of the above cyclic moieties such as aryloxy or heteroaryl amine shall be understood to mean an aryl, heteroaryl, heterocycle as defined above attached to it's respective functional group.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine except as otherwise noted.

DDQ—2,3-Dichloro-5,6-dicyano-1,4-benzoquinone;
PPA—Polyphosphoric acid;
HOAc—acetic acid;
RT or rt—room temperature;
n-BuLi—n-Butyllithium
DME—1,2-Dimethoxyethane
DMSO—Methyl sulfoxide
DMF—N,N-Dimethylformamide
DBU—1,8-Diazabicyclo[5.4.0]undec-7-ene
DMPU—N,N'-Dimethylpropyleneurea
HMPA—Hexamethylphosphoramide
TEA—Triethylamine
THF—Tetrahydrofuran.

The compounds of the invention are only those which are contemplated to be 'chemically stable' as will be appreciated by those skilled in the art. For example, a compound which would have a 'dangling valency', or a 'carbanion' are not compounds contemplated by the invention.

In order that this invention be more fully understood, the following examples are set forth in the overall reaction scheme below. These examples are for the purpose of illustrating preferred embodiments of this invention, and are not to be construed as limiting the scope of the invention in any way. Sample methods and starting materials to make compound (1) in Scheme I are shown in Examples 1 and 2 below.

EXAMPLES

SCHEME I

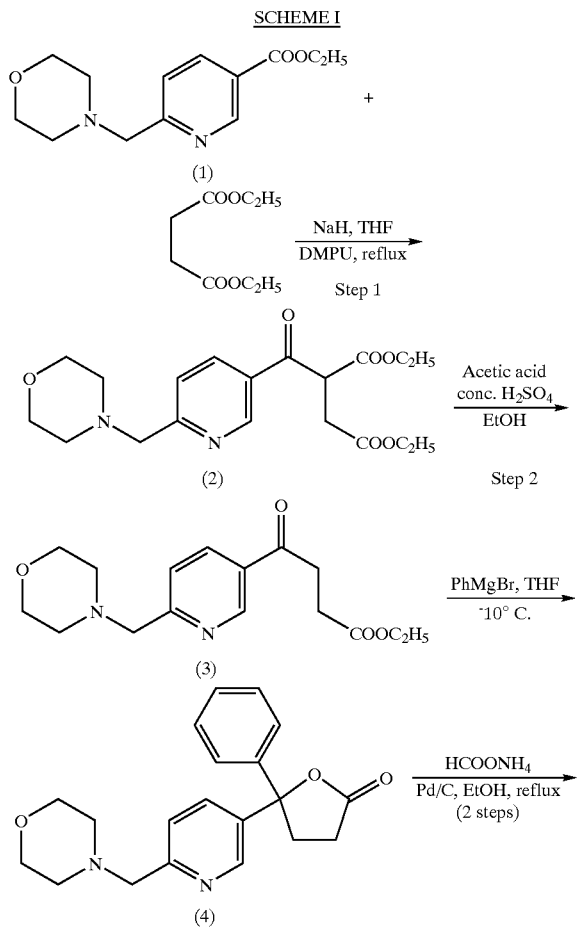

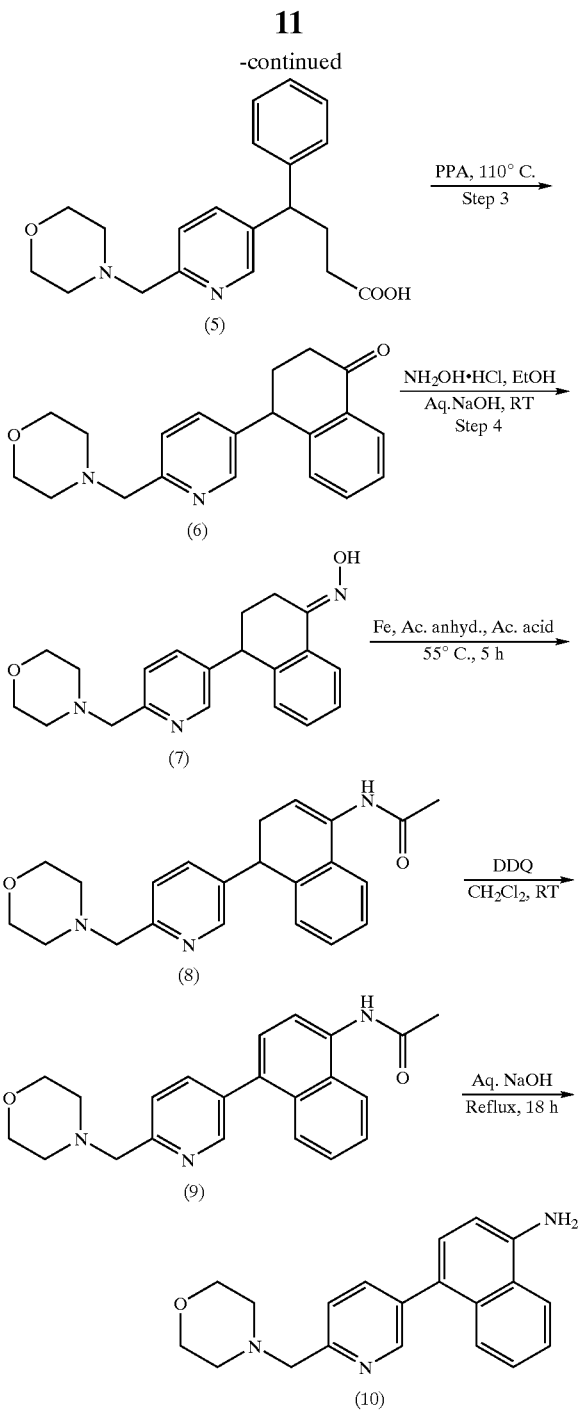

Example 1

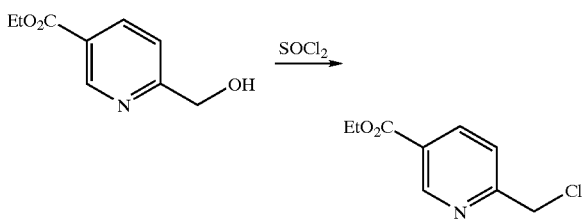

Preparation of chloride: A solution of alcohol shown above (18.0 g, 100 mmol) in 200 mL of $CH_2Cl_2$ was prepared and cooled in an ice-water bath. A solution of $SOCl_2$ (22 mL, 300 mmol) in 100 mL of $CH_2Cl_2$ was added to the above solution at the rate to keep the internal temperature below 10° C. After the addition, the cooling bath was removed and the reaction mixture was warmed to room temperature over 2 h. The reaction mixture was evaporated to remove all volatile by rotavap. The residue was dissolved in 150 mL of $CH_2Cl_2$ and saturated sodium bicarbonate solution was added until pH=9. The aqueous layer was extracted with $CH_2Cl_2$. The combined organic layers were dried ($MgSO_4$) and concentrated to give 20.0 g (100%) of the desired chloride. $^1$H NMR ($CDCL_3$): δ9.15 (s, 1H), 8.33 (d, J=8 Hz, 1H), 7.58 (d, J=8 Hz), 4.73 (s, 2H), 4.42 (q, J=7 Hz, 2H), 1.42 (t, J=7 Hz, 3H).

Example 2

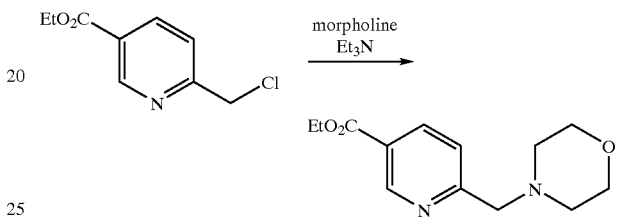

Preparation of morpholine moiety: A solution of chloride from Example 1 above (20 g, 100 mmol) and triethylamine (15.2 g, 150 mmol) in 125 mL of $CH_2Cl_2$ was prepared. 11 g (126 mmol) of morpholine was added and the reaction mixture was stirred at room temperature overnight (18 h). 100 mL of saturated sodium bicarbonate solution was added. The aqueous layer was extracted with $CH_2Cl_2$ (2×50 mL). The combined organic layers were dried ($MgSO_4$) and concentrated to give 24.3 g (97%) of desired product. $^1$H NMR ($CDCL_3$): δ9.15 (s, 1H), 8.25 (d, J=8 Hz, 1H), 7.52 (d, J=8 Hz, 1H), 4.40 (q, J=7 Hz, 2H), 3.73 (m, 6H), 2.51 (t, J=4 Hz, 4H), 1.40 (t, J=7 Hz, 3H).

Example 3

Diester (2). To a mixture of ester 1 (10.0 g, 40 mmol), diethyl succinate (7.0 g, 40 mmol) and sodium hydride (60% dispersion in mineral oil, 3.20 g, 80 mmol) in dry THF (200 ml) was added DMPU (20 ml) and methanol (0.10 ml) and the mixture was refluxed for 2.5 h. Additional diethyl succinate (10.50 g, 60 mmol) and sodium hydride (4.80 g, 120 mmol) were added in five equal portions to the refluxing reaction mixture at 0.75 h intervals. Refluxing was continued for additional 1.5 h. The cooled reaction mixture was poured into a stirring mixture of 2N HCl (200 ml) and ethyl acetate (200 ml). The aqueous phase was separated, the pH was adjusted to 8.5 with saturated sodium bicarbonate and it was extracted with ethyl acetate. The organic layer was washed with water and dried over anhydrous sodium sulfate. Evaporation of ethyl acetate gave almost pure 2 as yellowish brown oil (10.65 g, 70.4%). $^1$H NMR ($CDCl_3$) δ1.16 (t, J-=7.2 Hz, 3H), 1.22 (t, J=7.2 Hz, 3H), 2.51–2.53 (m, 4H), 3.02–3.20 (m, 2H), 3.72–3.75 (m, 6H), 4.10–4.15 (m, 4H), 4.78–4.80 (m, 1H), 7.58 (d, J=8.0 Hz, 1H), 8.27 (d, J=6.0 Hz, 1H), and 9.18 (d, J=2.1 Hz, 1H).

Example 4

Keto ester (3). Concentrated sulfuric acid (10 ml) was added carefully to the solution of the diester 2 (11.55 g, 30.5 mmol) in acetic acid (60 ml). The mixture was stirred at 100°

C for 6.5 h. After removing 30–40 ml of acetic acid under reduced pressure, ethanol (125 ml) was added to the residue and the reaction mixture was refluxed for 3.5 h. It was concentrated on a rotary evaporator followed by quenching with water. The mixture was extracted with ethyl acetate. The aqueous layer was separated, treated with saturated NaHCO$_3$ and extracted with methylene chloride. After drying over anhydrous sodium sulfate, the solvent was evaporated to give 3 as red viscous oil in practically pure state (8.35 g, 89%). Analytically pure sample was obtained from a silica gel column using ethyl acetate/hexane (1:1) as solvent for elution. $^1$H NMR (CDCl$_3$) δ1.27 (t, J=7.2 Hz, 3H), 2.50–2.53 (m, 4H), 2.76–2.79 (m, 2H), 3.28–3.31 (m, 2H), 3.72–3.75 (m, 6H), 4.15 (q, J=7.2 Hz, 2H), 7.56 (d, J=8.0 Hz, 1H), 8.21 (d, J=6.0 Hz, 1H) and 9.13 (d, J=2.0 Hz, 1H).

Example 5

Lactone (4). Phenylmagnesium bromide (1M/THF, 37.1 mmol, 37.1 ml) was added slowly to a stirring solution of the keto ester 3 (8.11 g, 26.5 mmol) in dry THF at −5° C. so that the reaction temperature stayed below 0° C. The reaction mixture was stirred at this temperature for additional 0.5 h. After quenching with 10% ammonium chloride solution, it was extracted with ethyl acetate, dried over anhydrous sodium sulfate and evaporated to give crude 4. An analytically pure sample was obtained from a silica gel column using ethyl acetate as solvent. $^1$H NMR (CDCl$_3$) δ2.47–2.49 (m, 4H), 2.58–2.62 (m, 2H), 2.92 (m, 2H), 3.62 (s, 2H), 3.70–3.72 (m, 4H), 7.29–7.42 (m, 6H), 7.69–7.71 (m, 1H) and 8.62 (d, J=2.0 Hz, 1H).

Example 6

Acid (5). To the solution of crude lactone 4 (from above) in reagent alcohol (100 ml) was added ammonium formate (5.0 g) and 10% Pd/C (0.66 g) and the reaction mixture was refluxed for 2.5 h. The catalyst was filtered and the filtrate was concentrated. A saturated solution of NaHCO$_3$ was added until the pH was 8.5. It was extracted with ethyl acetate to remove non-acidic impurities. The pH of the aqueous phase was then lowered to 6.5–7 with 2N HCl and it was extracted with CH$_2$Cl$_2$, dried over anhydrous sodium sulfate and concentrated to give 5 as light brown viscous oil (3.7 g, 41% over two steps). $^1$H NMR (CDCl$_3$) δ2.27–2.42 (m, 4H), 2.54–2.56 (m, 4H), 3.65 (s, 2H), 3.71–3.3.73 (m, 4H), 4.09–4.13 (m, 1H), 7.22–7.31 (m, 6H), 7.49–7.51 (m, 1H) and 8.51 (s, 1H).

Example 7

Tetralone (6). A mixture of acid 5 (3.6 g, 10.6 mmol) and polyphosphoric acid (85 g.) was stirred at 110° C. for 1.5 h. After cooling, the reaction mixture was quenched with cold water and treated with 2N NaOH to bring the pH up to ~5. It was extracted with CH$_2$Cl$_2$, dried over anhydrous sodium sulfate and evaporated to give almost pure ketone 6 as brown viscous oil (3.1 g, 90%). An analytically pure sample was obtained from preparative TLC using ethyl acetate as a solvent. $^1$H NMR (CDCl$_3$) δ2.23–2.35 (m, 1H), 2.45–2.78 (m, 7H), 3.68–3.77 (m, 6H), 4.32–4.36 (m, 1H), 6.94 (d, J=6.4 Hz, 1H), 7.34–7.7.47 (m, 4H), 8.13 (d, J=6.4 Hz, 1H) and 8.45 (d, J=2.0 Hz, 1H).

Example 8

Oxime (7). A solution of NaOH (1N, 17.6 ml, 17.6 mmol) was added to a stirring solution of hydroxylamine hydrochloride (1.19 g, 17.1 mmol) in water (10 ml) at 0° C. over five minutes followed by addition of the solution of ketone 6 (3.06 g, 9.5 mmol) in reagent alcohol (20 ml). After stirring the reaction mixture at room temperature for 18 h, it was diluted with water and extracted with methylene chloride. The organic layer was dried over anhydrous sodium sulfate and evaporated to give crude product. It was purified by silica gel chromatography using ethyl acetate as the solvent to give 7 as a colorless oil. It solidified on standing (2.00 g, 62%). $^1$H NMR (CDCl$_3$) δ2.02–2.12 (m, 1H), 2.16–2.26 (m, 1H), 2.50–2.60 (m, 4H), 2.70–2.90 (m, 2H), 3.7 (s, 2H), 3.72–3.78 (m, 4H), 4.15–4.20 (m, 4H), 6.90–6.95 (m, 1H), 7.20–7.35 (m, 3H), 7.98–8.02 (m, 1H), 8.4 (s, 1H) and 9.05 (bs, 1H).

Example 9

Amide (8). A solution of oxime 7 (1.42 g, 4.2 mmol) in acetic anhydride (15 ml) and acetic acid (1 ml, 16.8 mmol) was stirred at room temperature for 0.5 h. Iron powder (0.63 g, 10 mgatom) was added and the mixture was stirred at 55° C. for 5 h. The reaction mixture was cooled, ethyl acetate was added and the resulting mixture was filtered. The filtrate was evaporated to dryness. Water was added, the pH was adjusted to ~8 with 2N NaOH and again extracted with ethyl acetate. It was dried over anhydrous sodium sulfate and concentrated. The crude product was purified by silica gel chromatography eluting with 2.5% MeOH/CH$_2$Cl$_2$ to give 8 as yellow viscous oil (1.08 g, 71%). $^1$H NMR (CDCl$_3$) 2.18 (s, 3H), 2.50–2.51 (m, 4H), 2.63–2.66 (m, 2H), 3.62–3.73 (m, 6H), 6.30–6.31 (m, 1H), 6.87–6.97 (m, 2H), 7.14–7.33 (m, 5H), 7.51–7.53 (m, 1H) and 8.41 (bs, 1H).

Example 10

N-Acetyl naphthalene (9). A solution of amide 8 (0.36 g, 0.99 mmol) in methylene chloride (5 ml) was added fairly rapidly to a suspension of DDQ (0.34 g, 1.5 mmol) in methylene chloride (15 ml) at room temperature. After stirring the black reaction mixture for 0.25 h., it was quenched with NaOH (2N, 7 ml). The organic phase was separated, dried and evaporated to give yellow residue. It was passed through a plug of silica gel to give pure 9 (0.21 g, 59%). $^1$H NMR (CDCl$_3$) δ2.37 (s, 3H), 2.59–2.62 (m, 4H), 3.70–3.79 (m, 6H), 7.35–7.55 (m, 5H), 7.75–7.96 (m, 4H) and 8.66 (bs, 1H).

Example 11

Naphthyl amine (10). An aqueous solution of NaOH (3N, 6 ml) was added to a stirring solution of 9 (0.195 g, 0.54 mmol) in reagent alcohol (4 ml) and the mixture was refluxed for 5 h. The reaction mixture was cooled, diluted with water and extracted with methylene chloride. The organic layer was dried over anhydrous sodium sulfate and evaporated to give 10 as yellow foam (014 g, 80%). $^1$H NMR (CDCl$_3$) δ2.59–2.61 (m, 4H), 3.75–3.80 (m, 6H), 4.28 (bs, 2H), 6.85 (d, J=7.60 Hz, 1H), 7.23–7.26 (m, 1H), 7.44–7.51 (m, 3H), 7.75–7.77 (m, 1H), 7.82 (d, J=8.0 Hz, 1H), 7.89 (d, J=8.0 Hz, 1H) and 8.67 (d, J=2.0, 1H).

What is claimed is:

1. A process of making a compound of the formula(I):

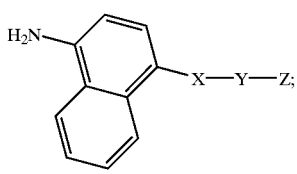

(I)

wherein:
the naphthyl ring is further optionally substituted by one or more $R_1$ or $R_2$;

X is chosen from
pyridinyl optionally independently substituted with one to three $C_{1-4}$ alkyl, $C_{1-4}$alkoxy, hydroxy, nitro, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is chosen from
$C_{1-4}$ unbranched carbon chain, $C_4$ branched or unbranched carbon chain and $C_{2-4}$ unsaturated carbon chain each optionally partially or fully halogenated;

Z is chosen from
morpholinyl optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, $CONH_2$, phenylamino-$C_{1-3}$ alkyl or $C_{1-3}$ alkoxy-$C_{1-3}$ alkyl; and halogen;

$R_1$ and $R_2$ are independently chosen from:
a $C_{1-6}$ unbranched alkyl optionally partially or fully halogenated, $C_{4-6}$ branched or unbranched alkyl optionally partially or fully halogenated, $C_{1-4}$ unbranched alkoxy, $C_4$ branched or unbranched alkoxy each being optionally partially or fully halogenated, halogen, $C_{1-3}$ alkyl-$S(O)_m$ optionally partially or fully halogenated and phenylsulfonyl;

m is 0, 1 or 2;
said process comprising:
i) reacting a Z—Y—X—COO—$R_x$ ester (II) with a di-ester (III), wherein $R_x$ in both (II) and (III) is independently $C_{1-5}$alkyl or aryl, in a suitable solvent and a suitable base and optionally in the presence of an additive at a temperature of about 0 to 200° C. for a reaction time of about 5 mm to 24 h, and isolating the compound intermediate (IV):

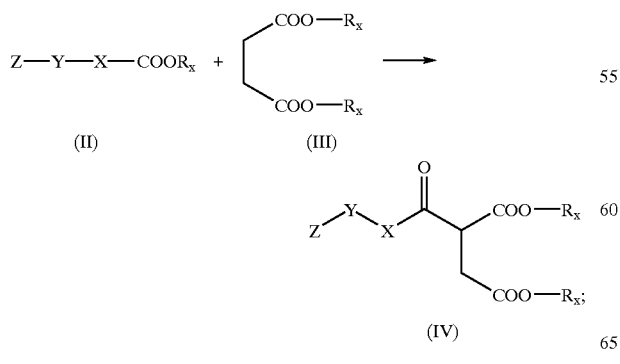

ii) hydrolysing the product of step i) with acidic or basic hydrolysis, and decarboxylating under suitable acid conditions at a temperature of about 50 to 200° C. and for about 5 mm to 24 hours; followed by esterifying under appropriate conditions with a $C_{1-5}$alcohol; subsequent phenyl nucleophilic addition wherein the phenyl is optionally independently substituted by $R_1$ and $R_2$; cleaving by reductive cleavage under appropriate conditions to form a carboxylic acid compound, and treating with a strong mineral acid optionally in a suitable solvent at RT to 200° C., to form a product intermediate of the formula(V), and isolating the product:

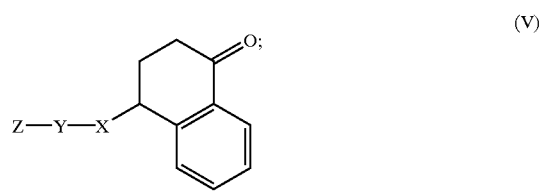

(V)

iii) reacting the product from step ii) with $HNR_yR_z$ or it's respective salt thereof, to form an enamine or imine compound of the formula(VI) under suitable conditions at about RT for about 1 to 24 h:

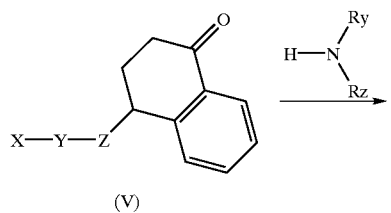

(V)

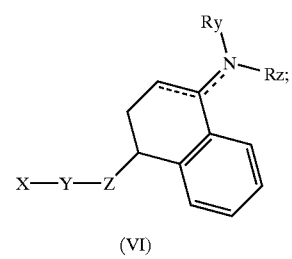

(VI)

wherein $R_y$ is $C_{1-5}$alkyl or hydrogen, $R_z$ is $C_{1-5}$alkyl, hydrogen or OH with the proviso that when formula (VI) is an enamine tautomer then $R_y$ and $R_z$ are both $C_{1-5}$alkyl, or when formula (VI) is an imine tautomer then $R_z$ is OH, $C_{1-5}$alkyl or hydrogen and $R_y$ is not present:

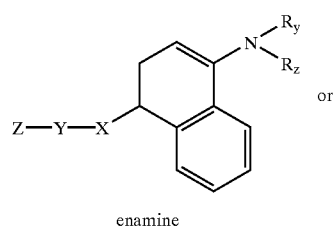

or enamine

[Structure: imine compound labeled "imine" with Z—Y—X substituent on dihydronaphthalene bearing =N—R_z]

iv) where the product of step iii) is an imine, in a one pot reaction acylating and reducing the product (VI); then treating the product of such reaction under oxidizing conditions capable of forming the naphthalene ring in the formula(I), followed by deprotecting under suitable conditions; or where the product of step iii) is an enamine, oxidizing the enamine under suitable oxidizing conditions to form the naphthalene ring, then deprotecting the amino nitrogen to form the formula (I):

[Structure (I): naphthalene with NH_2 and Z—Y—X substituents]

2. The process according to claim 1 wherein:
Y is
—CH$_2$—, and Z is morpholinyl.

3. The process according to claims 1 or 2 wherein:
in step i):
 R$_x$ is C$_2$H$_5$;
 the solvent is aprotic chosen from THF, DME, DMSO, ether, dioxane, CH$_2$Cl$_2$, CHCl$_3$, toluene, pyridine and DMF;
 the base is chosen from NaH, NaNH$_2$, Na t-butoxide, NaOH, pyridine, TEA, Na ethoxide, DBU and BuLi;
 the additive is chosen from DMPU and HMPA;
 and the reaction time is about 8 h;
in step ii):
 the hydrolysis is acidic;
 the decarboxylation acidic conditions are conc. H$_2$SO$_4$ in HOAc, the temperature is about 100° C. and the time is about 7 h;
 the esterification is with CH$_3$CH$_2$OH;
 the phenyl nucleophilic addition is via a phenyl Grignard reagent PhMgBr;
 the reductive cleavage is with HCOONH$_4$/Pd/C/EtOH;
 the added mineral acid is PPA and at a temperature of 110° C.;
in step iii):
 forming an oxime under oxime formation conditions by adding HNR$_y$R$_z$ wherein said HNR$_y$R$_z$ is the amine salt NH$_2$OH.HCl, in EtOH with NaOH for about 18 h;
in step iv):
 the product of step iii) is acetylated with acetic anhydride and acetic acid then reducing compound (VI) with Fe at about 55° C. for about 5 hours;
 the oxidizing conditions are treating the product with DDQ in a nonpolar solvent, at about 0 to 50° C., at about 0.5 to 10 h.

4. The process according to claim 3 wherein:
in step i):
 the solvent is THF;
 the temperature is 60–70° C.;
 the base is chosen from NaH and Na t-butoxide;
 the additive is DMPU; and
in step iv):
 for the for the oxidizing step the the nonpolar solvent is methylene chloride, the temperature is about RT and the time is about 5 h.

5. A compound chosen from:

[Morpholine-CH$_2$-pyridine-COOC$_2$H$_5$]

[Morpholine-CH$_2$-pyridine-C(O)CH$_2$CH$_2$-COOC$_2$H$_5$]

[Morpholine-CH$_2$-pyridine-C(O)CH(COOC$_2$H$_5$)CH$_2$COOC$_2$H$_5$]

[Morpholine-CH$_2$-pyridine-phenyl-substituted γ-butyrolactone]

[Morpholine-CH$_2$-pyridine-CH(Ph)CH$_2$CH$_2$-COOH]

[Morpholine-CH$_2$-pyridine-tetralone (ketone)]

[Morpholine-CH$_2$-pyridine-tetraline oxime (=N-OH)]

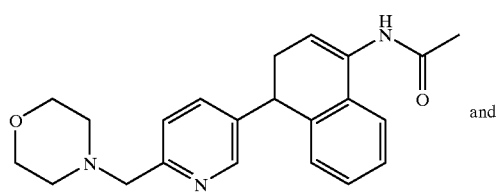
and
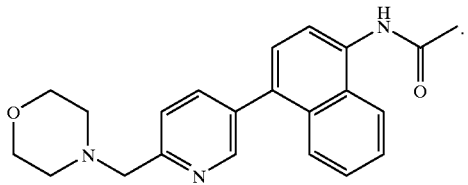
* * * * *